(12) United States Patent
Mauri et al.

(10) Patent No.: US 10,307,094 B2
(45) Date of Patent: Jun. 4, 2019

(54) MICROPERFUSION NEEDLE OR FISTULA NEEDLE WITH PROTECTIVE ELEMENT

(71) Applicant: Artsana S.p.A., Grandate CO (IT)

(72) Inventors: Elena Mauri, Grandate CO (IT);
Pierluigi Franco, Grandate CO (IT);
Daniele Pollaci, Grandate CO (IT)

(73) Assignee: PIKDARE S.R.L. (IT)

(*) Notice: Subject to any disclaimer, the term of this patent is extended or adjusted under 35 U.S.C. 154(b) by 20 days.

(21) Appl. No.: 15/202,895

(22) Filed: Jul. 6, 2016

(65) Prior Publication Data
US 2017/0014063 A1 Jan. 19, 2017

(30) Foreign Application Priority Data

Jul. 15, 2015 (IT) .................. 102015000034676

(51) Int. Cl.
*A61B 5/15* (2006.01)
*A61M 5/32* (2006.01)
(Continued)

(52) U.S. Cl.
CPC ........ *A61B 5/150664* (2013.01); *A61B 5/153* (2013.01); *A61B 5/15003* (2013.01); *A61B 5/15019* (2013.01); *A61B 5/15074* (2013.01); *A61B 5/150641* (2013.01); *A61M 5/158* (2013.01); *A61M 5/32* (2013.01); *A61M 5/321* (2013.01); *A61M 5/3271* (2013.01); *A61B 5/150259* (2013.01); *A61B 5/150389* (2013.01);
(Continued)

(58) Field of Classification Search
CPC ........................ A61M 25/0637; A61M 5/3271
See application file for complete search history.

(56) References Cited

U.S. PATENT DOCUMENTS

| 4,194,504 A * | 3/1980 | Harms ............... A61M 25/0014 |
| | | 604/165.03 |
| 5,085,639 A * | 2/1992 | Ryan .................... A61M 5/3243 |
| | | 604/110 |

(Continued)

FOREIGN PATENT DOCUMENTS

EP     2055344     5/2009

OTHER PUBLICATIONS

Italian Search Report of the Priority Italian Patent Application; dated Mar. 2, 2016.

*Primary Examiner* — Bhisma Mehta
*Assistant Examiner* — Matthew A Engel
(74) *Attorney, Agent, or Firm* — Adam K. Sacharoff; Much Shelist, P.C.

(57) ABSTRACT

A microperfusion needle or fistula needle with a protective element comprises a first component comprising a cannula, a body rigidly joined to the cannula, and having grasping wings extending therefrom, a second component comprising an elongate body having a cavity for slidably receiving the first component between an operating position of the cannula and a safety position of the cannula, the elongate body having lateral slots for the grasping wings to extend therethrough, the grasping wings being suitable for elastically bending around and contacting opposed portions of the elongate body. The elongate body comprises two arrays of projections, which are contacted by the wings when bent. Opposed pairs of projections are designed to contact and mechanically interfere with the grasping wings when bent.

8 Claims, 2 Drawing Sheets

(51) Int. Cl.
*A61B 5/153* (2006.01)
*A61M 5/158* (2006.01)

(52) U.S. Cl.
CPC .................. *A61B 5/150503* (2013.01); *A61M 2005/1586* (2013.01)

(56) References Cited

U.S. PATENT DOCUMENTS

| | | | | |
|---|---|---|---|---|
| 5,088,982 A * | 2/1992 | Ryan | ................... | A61M 5/3243 600/576 |
| 5,120,320 A * | 6/1992 | Fayngold | .......... | A61M 25/0637 604/174 |
| 5,192,275 A * | 3/1993 | Burns | ............... | A61M 25/0631 604/177 |
| 5,219,339 A * | 6/1993 | Saito | ................. | A61M 25/0631 604/177 |
| 5,382,240 A * | 1/1995 | Lam | .................. | A61M 25/0631 604/110 |
| 5,562,636 A | 10/1996 | Utterberg | | |
| 5,573,512 A * | 11/1996 | van den Haak | .... | A61M 5/3243 604/110 |
| 5,928,199 A * | 7/1999 | Nakagami | ............. | A61M 5/158 604/171 |
| 5,931,815 A * | 8/1999 | Liu | ................... | A61M 25/0637 604/171 |
| 7,377,911 B2 * | 5/2008 | Kunitomi | .......... | A61M 25/0631 604/177 |
| 7,753,878 B2 * | 7/2010 | Jones | .................... | A61M 5/158 604/110 |
| 2004/0153039 A1 | 8/2004 | Wang | | |
| 2004/0249346 A1* | 12/2004 | Kunitomi | .......... | A61M 25/0631 604/177 |
| 2007/0016148 A1* | 1/2007 | Iwase | .................... | A61M 5/158 604/264 |
| 2010/0049139 A1* | 2/2010 | Kiyono | ................. | A61M 5/158 604/180 |

* cited by examiner

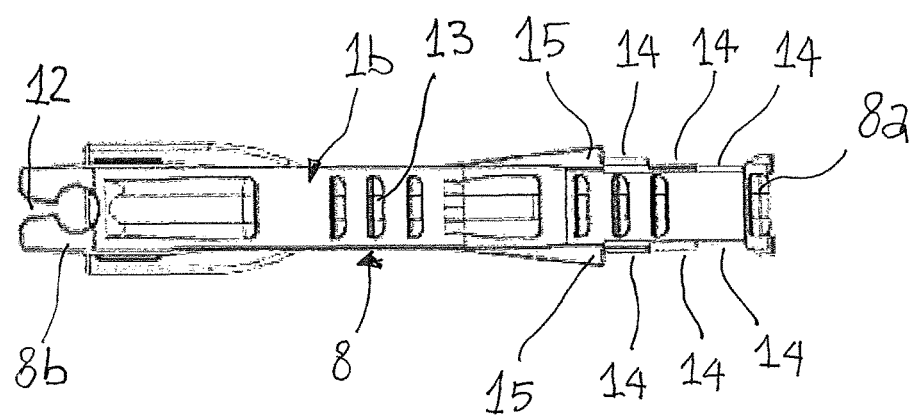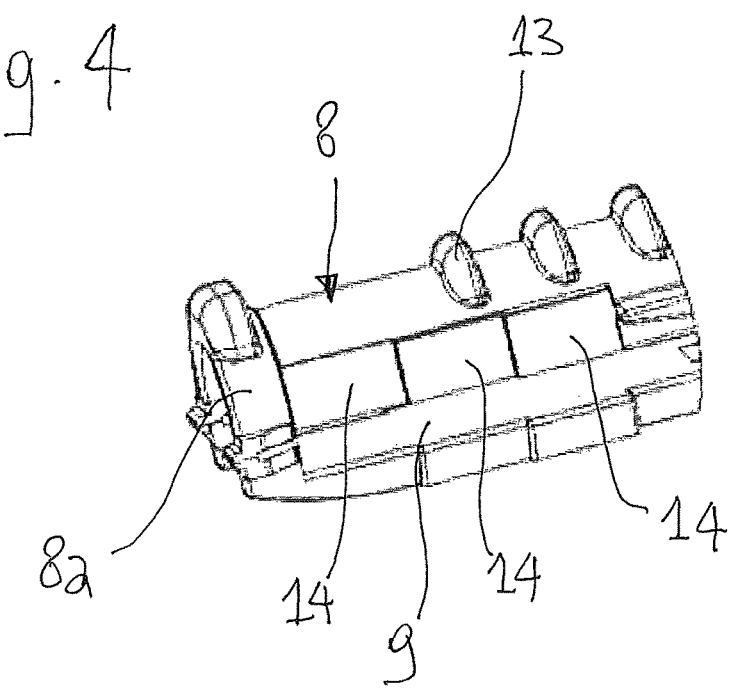

MICROPERFUSION NEEDLE OR FISTULA NEEDLE WITH PROTECTIVE ELEMENT

TECHNICAL FIELD

The present invention relates to a microperfusion needle or a fistula needle with a protective element for use in the medical field.

BACKGROUND OF THE INVENTION

A microperfusion needle is a medical instrument having a body with opposed lateral wings which is associated, on one side, with a tubular element and on the other side with a hollow cannula in fluid communication with the tubular element and adapted to be inserted into a vein of a patient to draw blood from him/her or introduce medicaments into the vein.

A fistula needle is a medical instrument having a body with opposed lateral wings which is associated on one side with a hollow cannula adapted to draw blood from the vein of a patient, and on the other side with a tube that carries such blood to a device known as dialyzer which, after purifying the blood, re-injects the blood into the patient through another tube and another fistula needle.

With a (microperfusion or fistula) needle as mentioned above, as an operator removes the cannula from the vein he/she is known to be exposed to injury and contact with the blood of the patient. In view of preventing infection spreading, the body of the aforementioned needle is known to be associated with an elongate protective element having a cavity, and adapted to receive the cannula once it has been removed from the vein of the patient. Therefore an assembly is obtained, which comprises two components, a first component defined by the (microperfusion or fistula) needle, having the body with the wings and the cannula, and a second component defined by the protective element.

In operation, i.e. when the cannula is introduced into the vein, the cannula projects out of the protective element. The entire assembly is moved during such introduction into the vein, by an action on the wings of the first component; as the cannula is removed from the blood vessel, the entire microperfusion needle (or fistula needle) is caused to slide in the cavity of the second component until the cannula is entirely covered thereby, to avoid any accidental contact with the operator.

A number of embodiments of protective elements as mentioned above are known in the art, and usually include a tubular body (defining the aforementioned cavity), which is open at two opposite ends and has lateral slots through which the wings of the first component can move to allow the cannula to fit into the cavity. These lateral slots also comprise specially shaped portions, which are designed to retain the wings of the first component therein, when the entire cannula is inserted in the second component. Thus, when the first component has to be made safe, it will be locked with respect to the second component and the cannula will be safely prevented from being contacted by the operator. One example of these devices is disclosed in EP 2055344 by the Applicant hereof.

Nevertheless, prior art solutions are still affected by the possibility that, when the entire assembly has to be moved, e.g. when the cannula is introduced into the vein, the (microperfusion or fistula) needle of the first component will slide in the second component (the protective element) or anyway a translational movement of the first component relative to the second component will occur, which may cause accidental injury to both the operator and the patient.

SUMMARY OF THE INVENTION

The object of the present invention is to provide a microperfusion or fistula needle with a protective element that can obviate the drawbacks of prior art arrangements.

Particularly, the object of the present invention is to provide a microperfusion or fistula needle with a protective element that ensures full control of the needle of the first component relative to the second component when the two components have to be moved in joined relationship to each other.

The above mentioned technical purpose and the specified object are substantially fulfilled by a microperfusion or fistula needle with a protective needle that incorporates the technical features as set forth in one or more of the annexed claims.

BRIEF DESCRIPTION OF THE DRAWINGS

Further features and advantages of the present invention will be more readily apparent upon reading of the illustrative, non-limiting description of a preferred non-exclusive embodiment of a microperfusion or fistula needle with a protective element as shown in the accompanying drawings, in which:

FIG. 3 is a plan view of one component of the needle of FIG. 1; and

FIG. 4 is a perspective view of a detail of the component of FIG. 3.

DETAILED DESCRIPTION OF THE INVENTION

Figure 1:
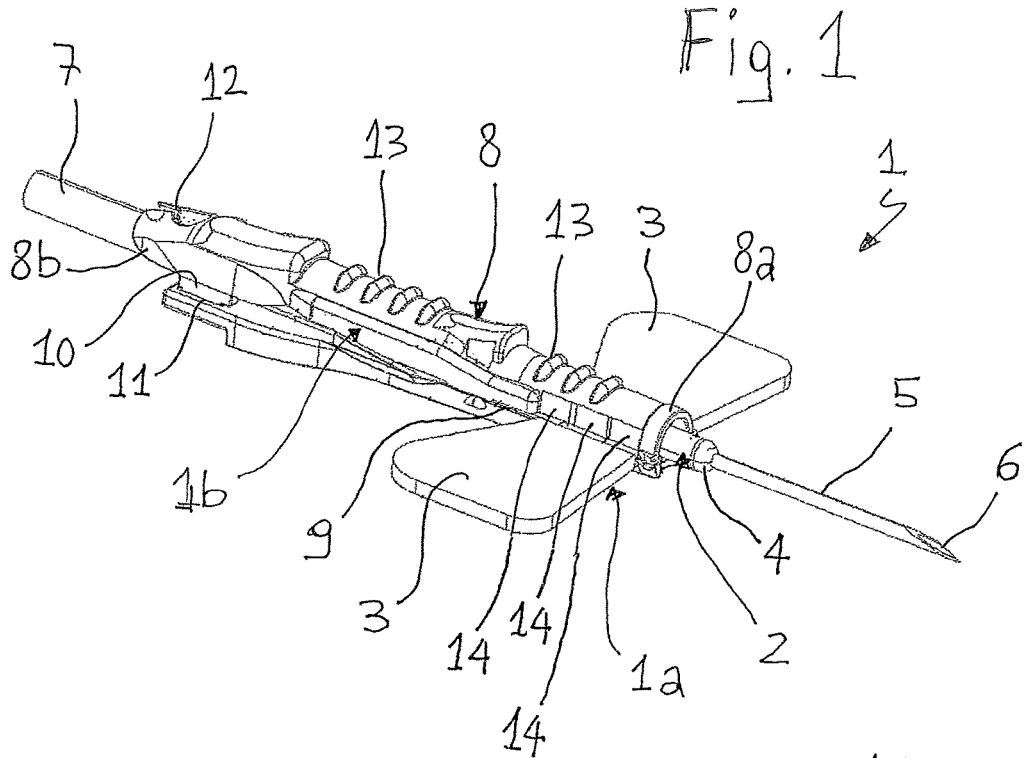
FIG. 1 is a perspective view of a microperfusion or fistula needle with a protective element of the present invention.

A microperfusion or fistula needle with a protective element has been generally designated by numeral 1 in the annexed drawings.

The microperfusion or fistula needle with the protective element comprises a first component 1a which includes a body 2 equipped with opposed grasping wings 3, and having a first end 4 with a cannula 5 connected thereto, the latter having a tip 6 (with a needle shield, not shown, possibly placed thereupon). A second end of the body 2 has a tube 7 associated therewith, which is in fluid communication with the cannula 5. In this respect, the body 2 is internally hollow to allow fluid communication between the cannula 5 and the tube 7. The latter may be connected to a bag or another reservoir containing a biological or medical fluid, or be connected to a bag for collecting blood drawn from a patient with the cannula 5 inserted in his/her vein 5.

In the preferred embodiment of the invention, the grasping wings 3 are formed of one piece with the body 2, although they might also be separated therefrom and mechanically connected thereto. The wings 3 are made of plastic and extend away from the body 2 to define respective substantially trapezoidal portions. The wings 3 are also formed with such a construction as to be elastically deformable (which means that their deformation disappears as the stress is released) and to bend relative to the body 2 and particularly to be able to pivot relative thereto substantially about axes parallel to the main direction of extension of the body 2 (which substantially coincides with the direction of extension of the cannula 5). The wings 3 are designed to be seized by the operator to be (elastically) bent and to move the cannula 5. The surfaces of the two wings 3 may be smooth or textured for improved grip for the fingers of the user.

Figure 2:
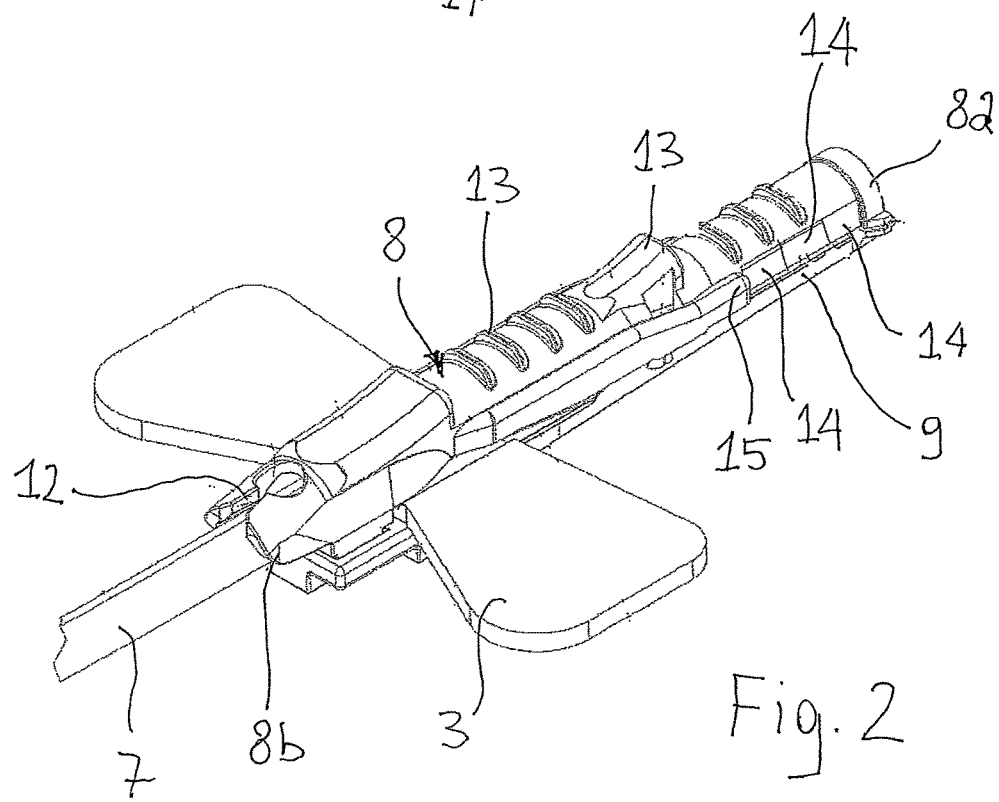
FIG. 2 is a perspective view of the needle of FIG. 1 in a different operating configuration.

The needle 1 also comprises a second component 1b which includes an elongate body 8 having a cavity for slidably receiving the first component 1a between an operating position in which the cannula 5 projects out of the cavity at a first end 8a of the elongate body 8 (as shown in FIG. 1) and a safety position in which the cannula 5 is entirely held within the cavity (as shown in FIG. 2). The elongate body 8 has lateral slots 9 for the grasping wings 3 to extend therethrough. The latter, as mentioned above, are adapted to be elastically bent about opposed portions of the elongate body 8, and thereby contact and encircle the latter. By releasing the wings 3, or anyway by releasing the force that causes the wings 3 to pivot, the latter tend to move back to the undeformed position (as shown in FIGS. 1 and 2), and the contact between the wings 3 and the elongate body 8 is lost. The elongate body is formed by stably coupling two half-parts that are hinged at the first end 8a of the body 8 (see FIG. 4) and rigidly joined to each other, at the second end 8b, by connecting arms 10 that project out of one half-part and fit into open connecting seats 11 in the other half-part (as schematically shown in FIG. 1). Thus, the grasping wings 3 are not allowed to slide out of the lateral slots 9 (between the two half parts), whereby the first component 1a cannot be separated (unless by breaking the needle and making it unusable) from the second component 1b of the needle.

At the second end 8b, the elongate body 8 comprises a slot 12 which terminates with a substantially circular cut-out for receiving the tube 7 of the first component 1a once the cannula 5 has been removed from the vein of the patient and moved to its safety position. When the first component 1a is in its safety position, the operator may insert the tube 7 into the slot 12 and into the circular cut-out to lock it by interference fit. Thus, the tube 7 will bend through 90° and be thereby occluded which will prevent any leakage of blood or fluid in the tube.

Preferably, the elongate body 8 comprises ribs or ridges 13 which are designed to provide a firm grip for the operator on the second component 1b and thereby facilitate retraction of the first component 1a when the cannula 5 has to be moved into its safety position. In this respect, when the first component 1a is in its safety position, retaining members are provided for stably retaining the cannula 5 in the cavity of the elongate body 8. These retaining members comprise, for example, projections of one of the two half-parts for abutment of openings and/or undercuts of the other half-part, which become stably coupled (by a pushing action of the operator or a translational movement of the body 2), thereby locking the first component 1a in the position so attained. Examples of retaining members that can lock the cannula 5 in the cavity of the body 2 are disclosed in EP 2055344A1.

Advantageously, the elongate body 8 comprises two arrays of projections 14 on the opposed portions of the elongate body 8, which are designed to be contacted by the wings 3 when the latter are elastically bent. Opposed pairs of projections 14 are designed to contact and mechanically interfere with the grasping wings 3 when bent. Thus, when the cannula 5 has to be moved while being joined to the elongate body 8, e.g. when the cannula is being introduced into the vein of the patient, the bent wings 3 are strongly hindered in their movement relative to the elongate body, which will prevent any relative sliding movement between the two components 1a, 1b. It shall be noted that the arrays of projections 14 are located proximate to the first end 8a of the elongate body 8, such that they face the wings 3 when the first component 1a is in its operating position, i.e. when the cannula 5 is entirely removed from the elongate body 8.

Since each array of projections has a plurality of projections 14, preferably at least two projections, the second component 1b may always be the same, irrespective of the sizes of the wings 3 in the direction parallel to the direction of extension of the elongate body 8. It shall be noted that, during manufacture of the needle 1, the need might arise of using first components 1a from different manufacturers, with wings of similar but different sizes. The plurality of projections 14 provide a plurality of mechanical interference fit areas, which will always ensure abutment of the wings, irrespective of their size.

Each projection 14 of the two arrays of projections defines an abutment shoulder for a wing 3, opposing the sliding motion of the first component 1a into the second component 1b. The projections 14 of an array of projections are successively arranged, with the projections farthest from the first end 8a of the elongate body 8 protruding out of the elongate body 8 to greater extents than the projections closer to the first end 8a of the elongate body 8 (as shown in FIG. 3). Preferably, the projections 14 of each array of projections have a step shape.

Preferably, a limit stop element 15 is provided in addition to the projections 14, and is placed on the elongate body 8 farther from the first end 8a of the elongate body than the above mentioned projections 14. The limit stop element 15 protrudes out of the elongate body to a greater extent than the projections 14 and ensures a safer lock of the first component 1a, should the wings 3 fail to be locked by the projections 14 during their translational movement in the elongate body 8, for any reason.

Of course, upon removal of the cannula 5 from the vein of the patient, the wings 3 will be simply pivoted to the undeformed position (or the force applied to the wings will be simply reduced) to release the mechanical interference fit provided by the projections 14 or by the limit stop element 15 and allow the first component 1a to slide in the second component 1b to the safety position.

We claim:

1. A microperfusion needle or fistula needle with a protective element, comprising:
   a first component which comprises:
      a cannula having a tip allowing insertion thereof into a vein of a patient, and
      a body rigidly joined to said cannula, the body having substantially opposed lateral grasping wings extending therefrom;
   a second component which comprises:
      an elongate body having a cavity for slidably receiving the first component between an operating position in which said cannula projects out of said cavity at a distal first end of the elongate body and a safety position in which said cannula is entirely held within said cavity, said elongate body having lateral slots for said grasping wings to extend therethrough, said grasping wings being configured to elastically bend around and contact opposed portions defined on the elongate body, and;
      two arrays of projections being positioned on said opposed portions of the elongate body, each of said two arrays of projections comprising individual projections, wherein each of the individual projections, of said two arrays of projections, being located proximal to said distal first end of the elongate body such that each and every individual projection abut said grasping wings only when the first component is in the operating position, and wherein the two arrays of projections are configured to contact and mechanically interfere with said grasping wings when the first component is in the operating position with the grasping wings bent, such that when the cannula is pushed proximally towards the elongate body, proximal movement of the grasping wings is hindered relative to the elongate body, such that relative proximal sliding movement between the first component and the second component is prevented, and when the grasping wings are undeformed, the first component is allowed to slide proximally from the operating position to the safety position, wherein said two arrays of projections are unable to contact and unable to mechanically interfere with the grasping wings when the first component is in the safety position.

2. The needle as claimed in claim 1, wherein each projection of said two arrays of projections defines an abutment shoulder for each grasping wing, each abutment shoulder opposing the sliding motion of the first component into the second component from the operating position to the safety position when abutted by a respective bent grasping wing.

3. The needle as claimed in claim 1, wherein each projection of an array of projections, defined from said two arrays of projections, are successively arranged; and wherein a projection farthest from the distal first end of the elongate body is configured to protrude out of said elongate body to greater extents than projections closer to said distal first end of the elongate body.

4. The needle as claimed in claim 1, wherein there are at least two projections in each of said two arrays of projections.

5. The needle as claimed in claim 1, comprising at least one limit stop element placed on said elongate body farther from said distal first end of the elongate body than said projections; said limit stop element protruding out of said elongate body to a greater extent than said projections to intercept said grasping wings when bent.

6. The needle as claimed in claim 1, wherein the projections of each of said two arrays of projections have a step shape.

7. The needle as claimed in claim 1, wherein said elongate body has ribs designed to facilitate retraction of the first component when the cannula is withdrawn from the vein.

8. The needle as claimed in claim 1, comprising retention members for stably retaining said cannula in said safety position.

* * * * *